United States Patent
Ohlander (10) Patent No.: US 9,167,338 B2
(45) Date of Patent: Oct. 20, 2015

(54) HEARING PROTECTOR

(71) Applicant: Hellberg Safety AB, Stenkullen (SE)

(72) Inventor: Joakim Ohlander, Hultafors (SE)

(73) Assignee: Hellberg Safety AB, Stenkullen (SE)

( * ) Notice: Subject to any disclaimer, the term of this patent is extended or adjusted under 35 U.S.C. 154(b) by 333 days.

(21) Appl. No.: 13/772,488

(22) Filed: Feb. 21, 2013

(65) Prior Publication Data

US 2013/0343559 A1 Dec. 26, 2013

(30) Foreign Application Priority Data

Jun. 21, 2012 (SE) ........................................ 1250675

(51) Int. Cl.
*H04R 1/10* (2006.01)
*H04R 1/28* (2006.01)

(52) U.S. Cl.
CPC ............ *H04R 1/1083* (2013.01); *H04R 1/2811* (2013.01); *H04R 1/1008* (2013.01); *H04R 1/2888* (2013.01)

(58) Field of Classification Search
None
See application file for complete search history.

(56) References Cited

U.S. PATENT DOCUMENTS

| 4,005,278 | A | 1/1977 | Görike | |
|---|---|---|---|---|
| 4,439,643 | A * | 3/1984 | Schweizer | 381/395 |
| 6,735,316 | B1 | 5/2004 | Wurtz | |
| 2005/0123161 | A1* | 6/2005 | Polany et al. | 381/334 |
| 2009/0010474 | A1 | 1/2009 | Ouryouji | |
| 2009/0279711 | A1* | 11/2009 | Heringslack | 381/71.6 |
| 2010/0128885 | A1* | 5/2010 | Roos et al. | 381/72 |
| 2011/0064239 | A1* | 3/2011 | Sjoman et al. | 381/72 |
| 2013/0129105 | A1* | 5/2013 | Hua | 381/71.6 |

FOREIGN PATENT DOCUMENTS

| EP | 0589623 | A2 | 3/1994 |
|---|---|---|---|
| EP | 0589623 | A3 | 3/1994 |
| WO | 2006118514 | A1 | 11/2006 |
| WO | 2008100197 | A1 | 8/2008 |
| WO | 2009139682 | A1 | 11/2009 |

OTHER PUBLICATIONS

European Search Report for EP application 13155939.5 mailed Jun. 17, 2014.
International Search Report for PCT application PCT/EP2013/062919 mailed Jun. 17, 2014.
Written Opinion of the International Search Authority for PCT application PCT/EP2013/062919 mailed Jun. 17, 2014.

* cited by examiner

*Primary Examiner* — Brenda Bernardi
(74) *Attorney, Agent, or Firm* — Polster, Lieder, Woodruff & Lucchesi, L.C.

(57) ABSTRACT

An ear cup for a hearing protection unit comprises a partition wall for separating a first part of the ear cup, facing the wearer, from a second part of the ear cup, facing the surroundings. A speaker is located in the first part of the ear cup and an electric connector is located in the second part of the ear cup. The speaker is mounted in a speaker holder, having a first cavity facing the ear of the wearer, to seal off a resonance space, the speaker holder in turn being arranged on the partition wall above a first aperture in the partition wall. Further, the speaker holder comprises a membrane above the first aperture. The speaker and the electric connector are connected by an electric cable, extending through the first aperture or through a second aperture in the partition wall. The speaker holder sealingly engages the electric cable.

11 Claims, 7 Drawing Sheets

Section view A-A
Scale: 2:1

FIG. 7

Section view A-A
Scale: 2:1

Front view
Scale: 2:1

FIG. 12

Section view A-A
Scale: 2:1

FIG. 13

Section view A-A
Scale: 2:1

Front view
Scale: 2:1

FIG. 18

Section view A-A
Scale: 2:1

FIG. 19

HEARING PROTECTOR

CROSS-REFERENCE TO RELATED APPLICATIONS

This application claims priority to Swedish Patent App. No. 1250675-4, filed Jun. 21, 2012, and which is incorporated herein by reference.

TECHNICAL FIELD OF THE INVENTION

The present invention relates to an ear cup, with an innercup space and an outercup space, separated by a partition wall, for a hearing protector, wherein the innercup space is provided with a speaker. In particular, the invention relates to improving the quality of sound reproduced by the speaker.

BACKGROUND

Hearing protectors are being used in environments where noise levels are high. Typically, hearing protectors comprise two ear cups and a device for fastening the hearing protector to the head of a wearer, so that the ear cups are positioned over the wearer's ears. Further, ear cups may be provided with active elements, such that the passive sound-reducing function is combined with the function of actively reproducing sound inside the ear cup to allow the user to hear this reproduced sound. Such an active elements typically include an electronic unit comprising a speaker.

The active element may incorporate different functions. One type of active element may, for instance, contain a radio receiver and the electronic circuitry required to reproduce the sound received by the radio receiver through the speaker. Another type of active element may be designed such that it is capable of reproducing ambient sound from the vicinity of the hearing protector. In this case, the hearing protector is typically provided with a microphone connected to the electronic unit. Another type of active element may enable communication with external devises connected to the hearing protector via electronic wire and/or wireless as via Bluetooth.

Electronic units provided with a speaker and a microphone have the function of receiving the sound from the microphone and converting it in such a manner that it is emitted by the speaker in the innercup at a level that conforms with relevant safety standards and is suitable for the wearer. Further, the electronic circuitry of the electronic unit typically comprises circuits for dampening frequencies and/or sound level that are particularly disturbing to the human ear for the benefit of the frequency range within which ordinary speech is situated. By such an arrangement, the wearer of an active hearing protector is able to talk to another person in a noisy environment without having to remove the hearing protector and without risking any hearing damage.

Evidently, the reproduced ambient sound will differ from the actually ambient sound, since some frequencies are being damped. Further, the reproduction of sound via a microphone-speaker arrangement will not be ideal. Thus, various measurements have been taken in the art to provide a good reproduction of ambient sound in ear cups provided with active sound reproducing arrangements.

WO 2008/100197 discloses an ear cup for a hearing protector, wherein the ear cup has noise-reducing space and at least one electronic unit with at least one speaker. Further, the ear cup has resonance space arranged to function as a sounding board for sound emitted by the speaker. By providing a closed resonance space the speaker is stated to provide a better bass sound.

WO 2006/118514 discloses an ear cup for a hearing protection unit which comprises an inner cup portion, which defines a noise damping space facing towards the user. The ear cup further has an outer cup portion for accommodating electronics and/or an electrical current source. The inner cup portion and the outer cup portion are separated by a partition which is of one-piece manufacture with the inner cup portion. The partition is substantially closed, with the exception of an opening in which a fixing portion on a bracket is disposed. The fixing portion is included/integrated with conductors to a loudspeaker. The bracket also has a baffle plate which extends along the periphery of the loudspeaker. The baffle plate is stated to improve the sound reproduction in lower frequency ranges. In this context, it is important to notice that the baffle plate does not, on its-rear side, screen off or possibly more or less seal off a volume that could reduce the size of the effective noise damping space. Although, the baffle plate is stated to improve the sound reproduction the provided solution, it is a space requiring solution. Further, the baffle may be uncomfortable for people having outstanding ears.

WO 2009/139682 discloses a hearing protector having two closed muffs which sealingly abut against the wearer's head, so that there is formed a closed space in each muff and about the user's ear. A loudspeaker is disposed interiorly in the muff and has a membrane whose one side is turned to face towards the user's ear, and whose opposing side is turned to face towards a closed volume which is defined by the membrane and an enclosure. In order to improve the base reproduction in listening to music, the interior of the enclosure is, via at least one hole or one duct, in flow communication with the ambient surroundings outside of the closed space of the muff. Although, the base reproduction is improved, the presence of a hole or a duct will imply that ambient noise may "leak" into the noise damping space.

SUMMARY OF THE INVENTION

Consequently, the present invention seeks to mitigate, alleviate, eliminate or circumvent one or more of the above-identified deficiencies in the art and disadvantages singly or in any combination by an ear cup for a hearing protection unit. The ear cup comprises a partition wall for separating a first part of the ear cup, facing the wearer, from a second part of the ear cup, facing the surroundings; a speaker located in the first part of the ear cup; wherein the speaker is mounted in a speaker holder, having a first cavity facing the wearer, to seal of a resonance space; the speaker holder in turn being arranged on the partition wall above a first aperture in the partition wall; wherein the speaker holder comprises a membrane extending across the first aperture; and an electric connector located in the second part of the ear cup, the speaker and the electric connector being connected by an electric cable.

Further advantageous features of the invention are defined in the dependent claims. In addition, advantageous features of the invention are elaborated in embodiments disclosed herein.

BRIEF DESCRIPTION OF THE DRAWINGS

The invention will below be described more in detail, having reference to a preferred embodiment thereof shown on the accomplishing drawings, in which.

DETAILED DESCRIPTION OF PREFERRED EMBODIMENTS

Figure 1:
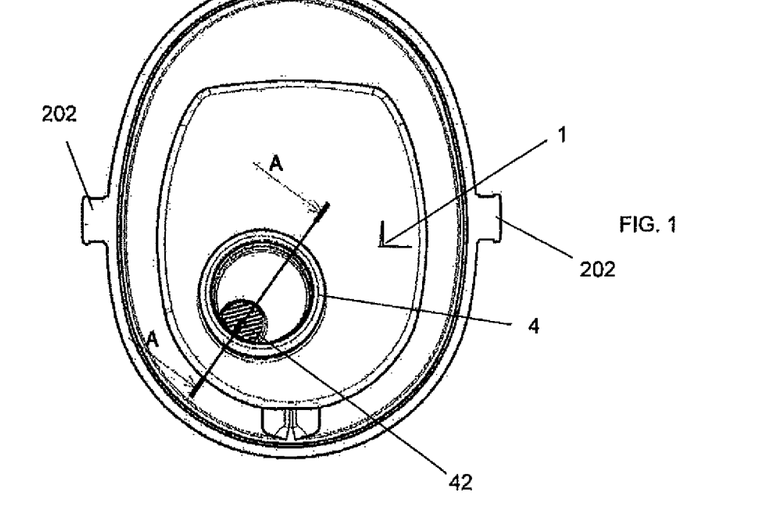
FIG. 1 shows the side of the ear cup, according to an embodiment, intended to face the wearer, without the speaker.
Figure 7:
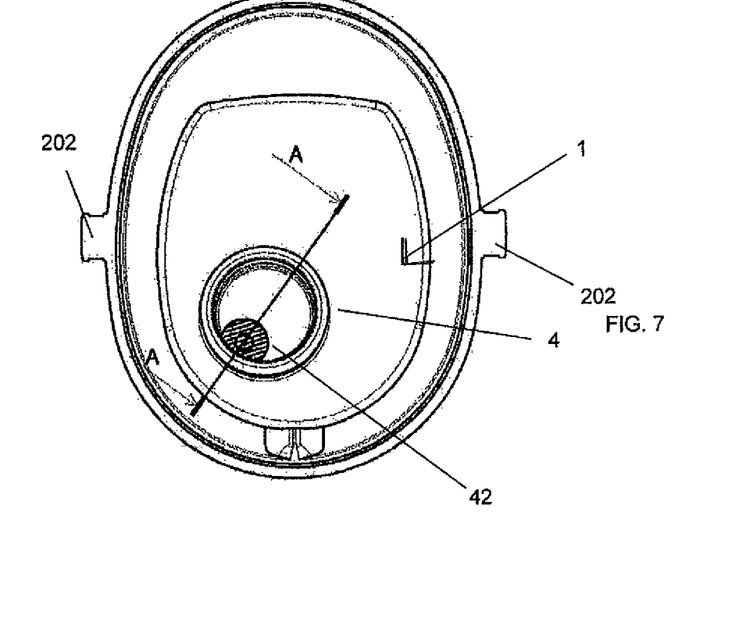
FIG. 7 shows the side of the ear cup, according to an embodiment, intended to face the wearer, without the speaker.
Figure 13:
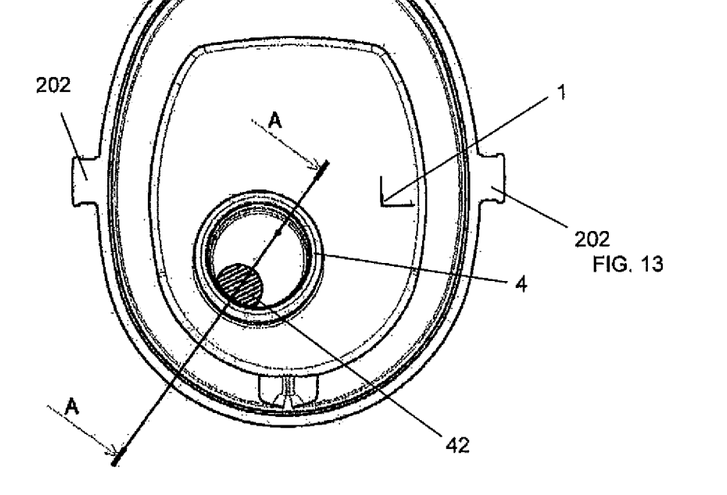
FIG. 13 shows the side of the ear cup, according to an embodiment, intended to face the wearer, without the speaker.

The present invention relates to an ear cup to form part of a hearing protector (cf. FIG. 19), in accordance with FIGS. 1, 7 and 13. Hearing protectors typically comprise two ear cups, one for each ear. The ear cups are arranged on a support 200, which may be mounted on a helmet, or neckband or headband type support. By means of the support 200, the ear cups are pressed over the ears to seal off a noise attenuating space. Typically the ear cups are provided with a sealing ring 201 arranged at the periphery of the ear cup.

According to an embodiment, the invention relates an ear cup, comprising a rigid partition wall 1, to form part of a hearing protector. The rigid partition wall 1 is typically made of a thermoplastic, such as acrylonitrile butadiene styrene (ABS), polypropylene (PP), polyoxymethylene (POM), and combinations thereof. As the rigid partition wall 1 is to be part of a hearing protector with active elements, such as elements for reproducing ambient sound from the vicinity of the hearing protector or elements with radio function, a speaker 2 and electric connector 3, which may be connected to a microphone or a radio receiver, are arranged on opposite sides of the partition wall 1.

The speaker 2 is mounted in a speaker holder 4 made of an elastic material and positioned on the side of the partition wall 1 intended to face the ear of the wearer of the hearing protector. Examples of suitable elastic materials include thermoplastic elastomers, e.g. thermoplastic polyurethanes (TPU), and thermoset elastomers, e.g. rubber and silicon rubber. In order to provide a resonance space 8, the speaker holder 4 has a first cavity 44 facing the ear of the wearer. The first cavity 44 is sealed off by the speaker 2 to provide the resonance space 8. In order to improve the quality of sound from loudspeaker and to the control low frequency base sound reproduced from the loudspeaker, the speaker holder 4 is arranged on the partition wall 1 above a first aperture 13 in the partition wall 1. The part of the speaker holder 4 overlaying the aperture 13 is arranged to form a flexible membrane 42, thereby minimizing "leakage" of ambient noise into the noise damping space via the first aperture 13. The flexible membrane 42 is thus located behind the speaker 2, i.e. on the other side of the speaker 2 in relation the user. The flexible membrane 42 may thus be a part of the speaker holder 4.

The speaker 2 and the electric connector 3 are connected by an electric cable 31 running through an aperture in the partition wall 1. The aperture through which the electric cable 31 runs has an aperture area that is larger than the transverse cross-section of the electric cable 31, such that the electric cable may run freely through the aperture. Since normally both the aperture and the electric cable 31 have a circular shape in the transverse plane, the diameter of the aperture is greater than the diameter of the cable.

Figure 2:
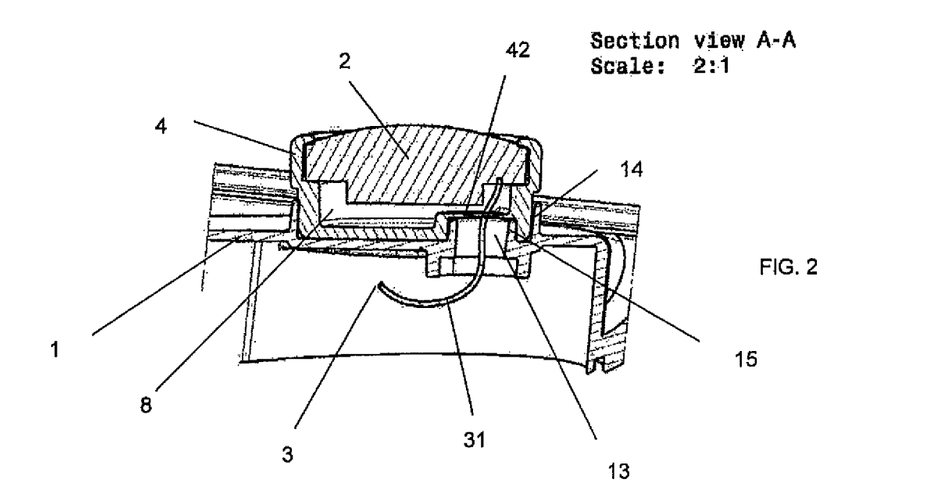
FIG. 2 shows a cross-section of the ear cup taken along line A-A in FIG. 1, in which the speaker, the speaker holder, and the membrane are shown.
Figure 3:
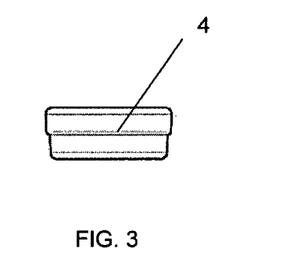
FIGS. 3-6 show various views of the speaker holder of FIG. 2.
Figure 4:
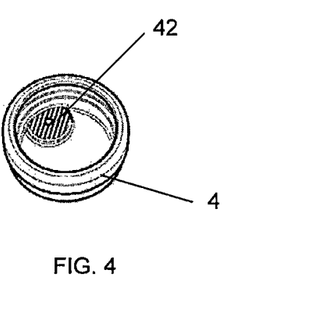
Figure 5:
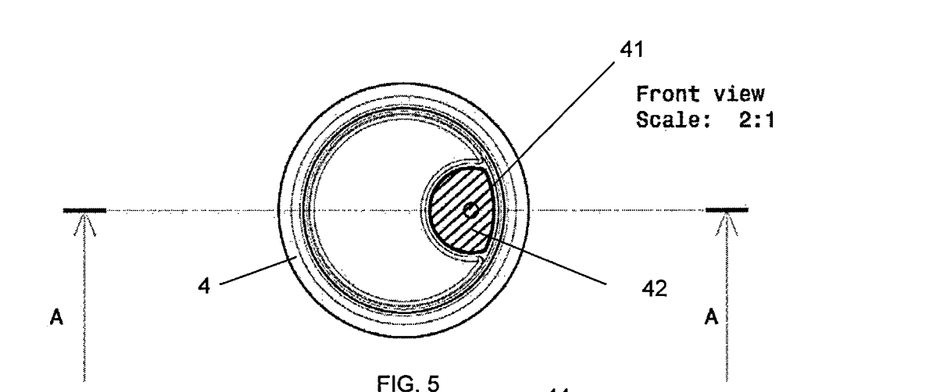
Figure 8:
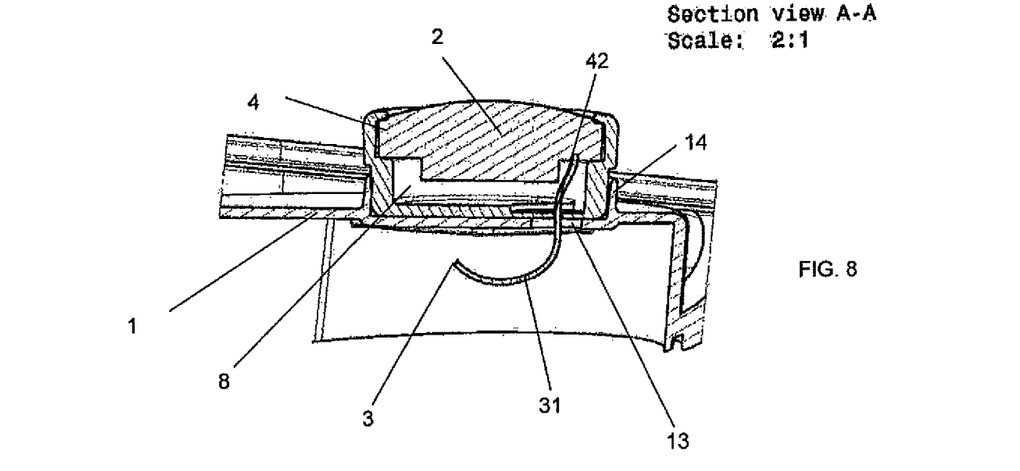
FIG. 8 shows a cross-section of the ear cup taken along line A-A in FIG. 7, in which the speaker, the speaker holder, and the membrane are shown.
Figure 9:
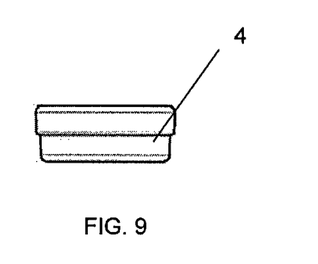
FIGS. 9-12 show various views of the speaker holder of FIG. 8.
Figure 10:
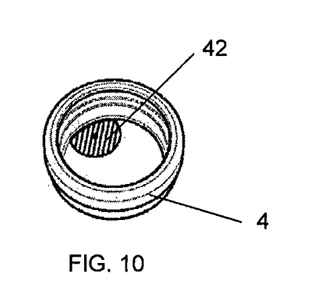
Figure 11:
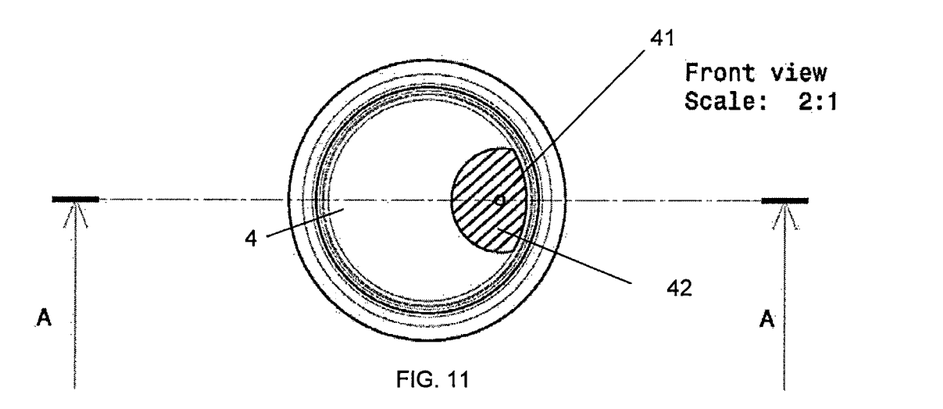
Figure 12:
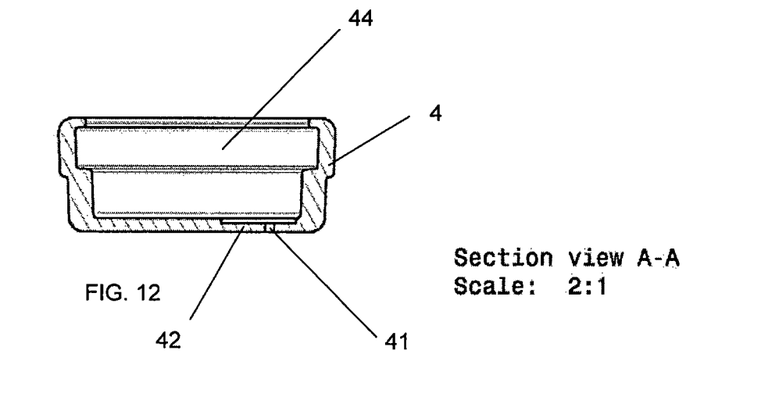
Figure 14:
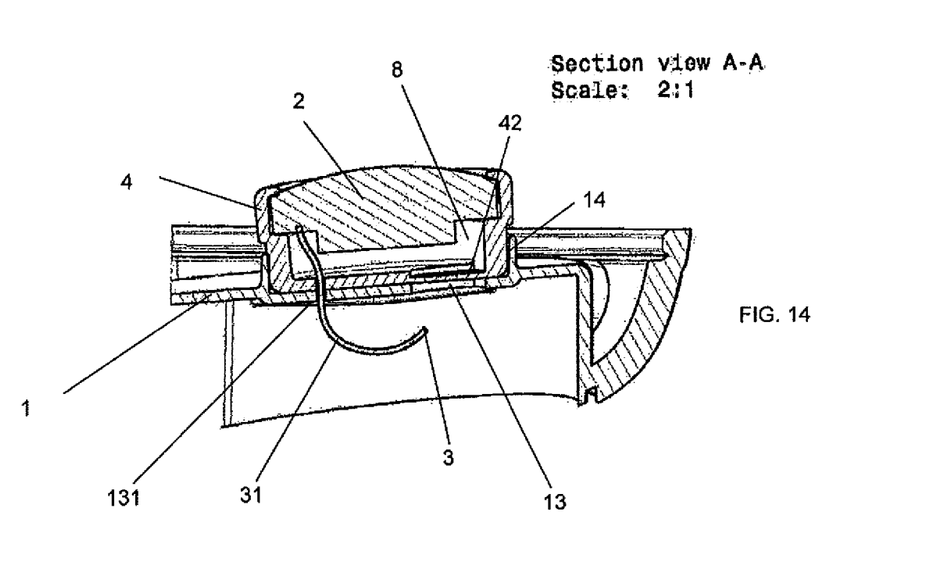
FIG. 14 shows a cross-section of the ear cup taken along line A-A in FIG. 13, in which the speaker, the speaker holder, and the membrane are shown.
Figure 15:
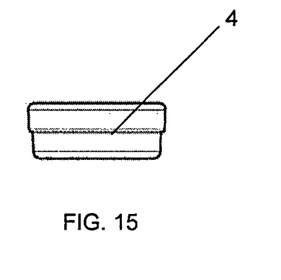
FIGS. 15-18 show various views of the speaker holder of FIG. 14.
Figure 16:
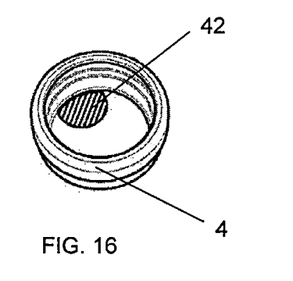
Figure 17:
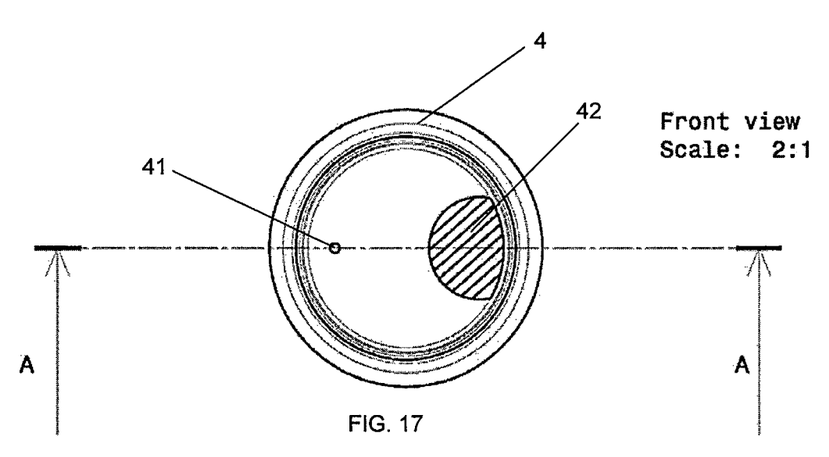
Figure 18:
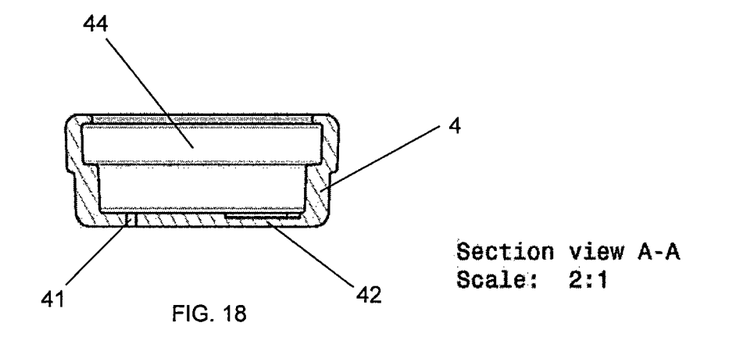

According to an embodiment, the electric cable 31 runs through the first aperture 13 in the partition wall 1 (cf. FIGS. 2 and 8). According to alternative embodiment, the electric cable 31 runs through a second separate aperture 131 in the partition wall 1 (cf. FIG. 14).

Since the speaker 2 is connected to the electric connector 3 by an electric cable 31, the speaker holder 4 is provided with a cable hole 41, through which the electric cable 31 runs. The cable hole 41 may be superimposed over the first aperture 13 (cf. FIGS. 2 and 8), or alternatively over the second separate aperture 131 (cf. FIG. 14), if present. The cable hole 41 is further adapted to sealingly engage with the electric cable 31, thereby minimizing "leakage" of ambient noise into the noise damping space.

According to an embodiment, the electric connector 3 is connected to a microphone. Typically, the electric connector 3, according to such an embodiment, is connected to an electronic circuitry, comprising circuits for dampening frequencies that are particularly disturbing to the human ear for the benefit of the frequency range within which ordinary speech is situated, which electronic circuitry in turn is connected to the microphone.

According to an embodiment, the partition wall 1 has a first collar 14 for suspending the speaker holder 4, in which the speaker 2 is mounted. The first collar 14 is arranged around the aperture 13 on the side of the partition wall 1 intended to face the ear of the wearer of the hearing protector. The first collar 14 is adapted in shape and size to the periphery of the speaker holder 4, such that the speaker holder 4 may be removably slipped into the first collar 14 to achieve an engagement between the speaker holder 4, and thus the speaker, and the partition wall 1. Hence, the first collar 14 forms a protrusion in which the speaker holder 4 may be suspended (cf. FIGS. 2, 8 and 14).

The speaker holder 4 is mounted in the first collar 14 to provide a suspension for the speaker 2, such as disclosed above. The part of the speaker holder 4 that is positioned over the first aperture 13 is thin, as to form a flexible membrane 42. The thickness of the membrane is preferably from about 0.5 mm to about 1 mm. When the thickness is above about 1 mm, too much low frequency sound disappears. When the thickness is below about 0.6 mm, too much low frequency sound passes. The flexible membrane 42 may improve the function of the resonance space 8 and thereby the sound reproduction. Further, the flexible membrane 42 may transfer air vibrations from the resonance space 8 to the outercup space, whereby improving the quality of sound from loudspeaker and controlling low frequency base sound reproduced by the loudspeaker. Importantly, the flexible membrane 42 will also minimize "leakage" of ambient noise into the noise damping space via the first aperture 13. The flexible membrane 42 may be circular. Further, also the first collar 14 may be circular.

While the first collar 14 may be ring shaped and have a continuous wall, it is not necessary for the wall to be continuous as the resonance space 8 is, in any event, sealed off by the speaker 2 and the speaker holder 4. Thus, the collar may be provided with slits or a number of separated rings segments, to minimize production material. Further, it may be easier to snapp the speaker holder 4 into engagement with the second collar 15, if the second collar 15 is comprised of separated rings segments.

According to an embodiment, the aperture 13 is not positioned centrally of the first collar 14, thereby facilitating the positioning of the speaker holder 4 upon assembling the ear cup. Further, such an arrangement will prevent the speaker holder 4 from rotating in the first collar 14. Rotation of the electric cable 31 may eventually cause line breakdown.

According to an embodiment, the membrane 42 is arranged in a protrusion from the speaker holder 4. The protrusion corresponds in shape and size to the first aperture 13 and is inserted into the first aperture 13, whereby the speaker holder 4 is mounted on the partition wall 1 above a first aperture 13.

Figure 6:
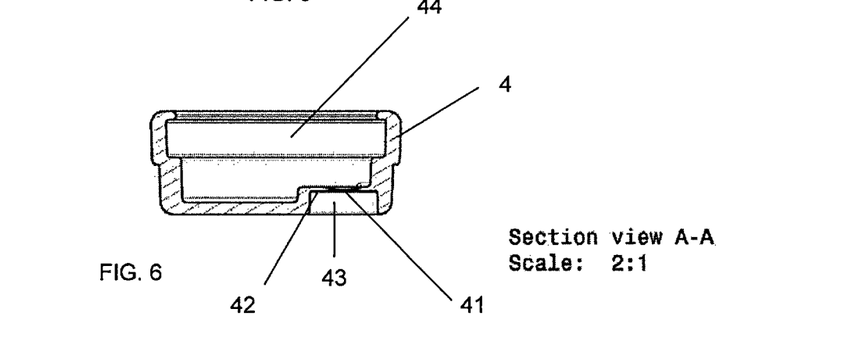

According to an embodiment, the partition wall 1 has a second collar 15 (cf. FIG. 2). The second collar 15 is arranged around the first aperture 13 on the side 12 of the partition wall intended to face the ear of the wearer of the hearing protector. If present, the first collar 14 encloses the second collar 15. According to such an embodiment, the speaker holder 4 has a second cavity 43 facing away from the ear of the wearer (cf. FIG. 6). The shape and size of the second cavity 43 corresponds to the size and shape of the second collar 15, whereby the speaker holder 4 may be slipped onto the second collar 15 to secure the position of the speaker holder 4.

The ear cup may further be provided with an arrangement of a spacer and sealing ring 201 at the periphery of the rigid partition wall 1. When a hearing protector comprising the ear cup is worn, the partition wall 1 and a spacer with a sealing ring 201 seals off a noise attenuating space. Further, the ear cup may have a lid which, together with the partition wall 1, encloses an outercup space housing the electric connector 3. The outercup space may be arranged to accommodate an electric unit connected to the electric connector 3. As the electric unit may comprise a microphone to register ambient sounds, in order to allow for the microphone to reproduce them, the outercup space is typically in flow communication with, or open to, the surrounding area. The sealing ring 201 normally comprises a soft foam material, which may be compressed under pressure to expand once the pressure is removed. Further, the sealing ring 201 may comprise a sealing lip of an elastomeric material. In order to increase the damping of ambient sound, the part of the ear cup sealing of the noise damping space may be lined with a noise absorbent, such as a foamed material. Further, the ear cup may be provided with a means 202 for attaching it to a support 200, such as for mounting on a helmet, or a neck- or headband type support.

Figure 19:
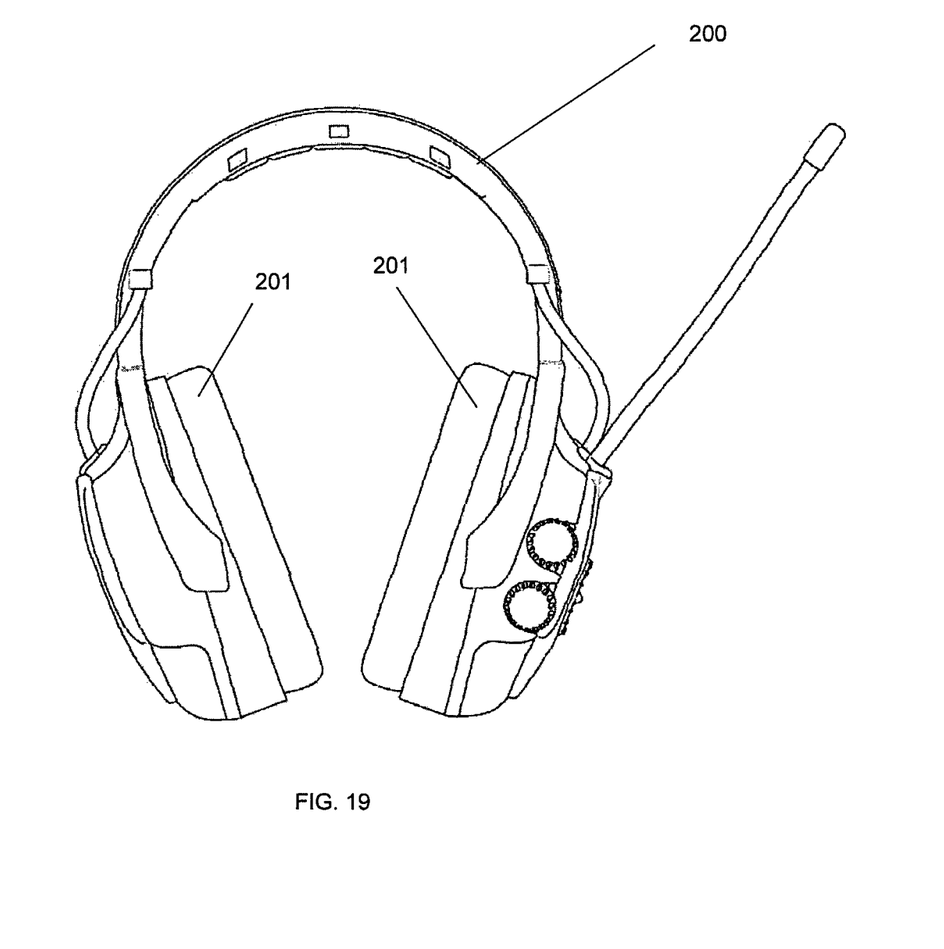
FIG. 19 shows a hearing protector.

According to another embodiment, depicted in FIG. 19, the invention relates to a hearing protector comprising two ear cups as herein above described. The ear cups are connected by a support 200, such as a helmet, a neckband or a headband.

Without further elaboration, it is believed that one skilled in the art can, using the preceding description, utilize the present invention to its fullest extent. The preferred specific embodiments described herein are, therefore, to be construed as merely illustrative and not limitative of the description in any way whatsoever. Further, although the present invention has been described above with reference to specific embodiments, it is not intended to be limited to the specific form set forth herein. Rather, the invention is limited only by the accompanying claims and, embodiments other than the specific embodiments described above are equally possible within the scope of these appended claims, e.g. different than those described above.

In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous.

In addition, singular references do not exclude a plurality. The terms "a", "an", "first", "second" etc do not preclude a plurality.

The invention claimed is:

1. An ear cup for a hearing protection unit, said ear cup comprising:
    a partition wall for separating a first part of the ear cup from a second part of the ear cup; the first part of the ear cup facing a wearer when the wearer wears the ear cup and the second part of the ear cup facing the surroundings;
    a speaker located in the first part of the ear cup;
    wherein the speaker is mounted in a speaker holder, the speaker holder having a first cavity facing the wearer when the ear cup is worn, to seal off a resonance space; said speaker holder in turn being arranged on the partition wall above a first aperture in the partition wall;
    wherein the speaker holder comprises a flexible membrane that transfers air vibrations extending across the first aperture; and
    an electric connector located in the second part of the ear cup; said speaker and said electric connector being connected by an electric cable.

2. The ear cup according to claim 1, wherein the electric cable extends freely through said first aperture in the partition wall, or through a second separate aperture in the partition wall; said speaker holder sealingly engaging with the electric cable.

3. The ear cup according to claim 1, wherein the partition wall has a first collar arranged around the aperture on the side of the partition wall intended to face the ear of the wearer and being adapted in shape and size to correspond to the shape and size of the speaker holder; and
    wherein the speaker holder is received by the first collar, whereby the first collar provides a suspension for the speaker holder.

4. The ear cup according to claim 1, wherein said flexible membrane is circular.

5. The ear cup according to claim 1, wherein the electric cable extends freely through said first aperture.

6. The ear cup according to claim 1, wherein said speaker holder is made of an elastomer; and said partition wall is made of a thermoplastic.

7. The ear cup according to claim 1, wherein the partition wall has a second collar arranged around the aperture on the side of the partition wall intended to face an ear of the wearer when the ear cup is worn;
    said first collar being arranged around said second collar;
    said speaker holder having a second cavity facing away from the ear of the wearer when the ear cup is worn and being adapted in shape and size to correspond to the shape and size of the second collar; and
    wherein the speaker holder is received in the second collar, whereby the second collar secures the position of the speaker holder.

8. The ear cup according to claim 1, wherein said ear cup further comprises a spacer and a sealing ring arranged at the periphery of the rigid partition wall, wherein the partition wall and the sealing ring seal off a noise damping space when placed over the ear of a wearer; and the part of the ear cup sealing off the noise damping space is lined with a noise absorbent material.

9. The ear cup according to claim 1, wherein said ear cup further comprises a lid, said lid, together with said partition wall, enclosing an outercap space adopted to accommodate an electric unit connected to said electric connector.

10. The ear cup according to claim 9, wherein said electric unit comprises a microphone.

11. A hearing protector comprising two ear cups according to claim 1, the ear cups being connected by a support.

\* \* \* \* \*